(12) United States Patent  (10) Patent No.: US 7,635,352 B2
Adams  (45) Date of Patent: Dec. 22, 2009

(54) CATHETER AND INTRODUCER NEEDLE ASSEMBLY WITH NEEDLE SHIELD

(75) Inventor: Chad Adams, Cedar Hills, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 424 days.

(21) Appl. No.: 11/138,215

(22) Filed: May 27, 2005

(65) Prior Publication Data

US 2006/0270991 A1 Nov. 30, 2006

(51) Int. Cl.
*A61M 5/178* (2006.01)
(52) U.S. Cl. .................................. 604/164.08
(58) Field of Classification Search .................. 604/192, 604/164.08, 164.01
See application file for complete search history.

(56) References Cited

U.S. PATENT DOCUMENTS 6,638,252 B2 * 10/2003 Moulton et al. ........ 604/164.01

FOREIGN PATENT DOCUMENTS

| EP | 0352928 A1 | 1/1990 | |
|---|---|---|---|
| WO | 0123028 A1 | 4/2001 | |
| WO | WO 01/23028 | * 4/2001 | ................. 604/192 |
| WO | 0245786 A1 | 6/2002 | |
| WO | 0245786 A3 | 6/2002 | |
| WO | WO 0245786 | * 6/2002 | |

OTHER PUBLICATIONS

EP06114444-European Search Report.

* cited by examiner

*Primary Examiner*—Kevin C Sirmons
*Assistant Examiner*—Deanna K Hall
(74) *Attorney, Agent, or Firm*—Kinney & Lange, P.A.

(57) ABSTRACT

An assembly with a needle shield is provided. The needle shield includes a lock for preventing unwanted proximal and distal movement of the needle once the needle has been withdrawn into the needle shield.

23 Claims, 11 Drawing Sheets

CATHETER AND INTRODUCER NEEDLE ASSEMBLY WITH NEEDLE SHIELD

FIELD OF THE INVENTION

The subject invention relates to an assembly that will safely shield a distal tip of a sharp.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Catheters, particularly intravascualar (IV) catheters, are used for infusing fluid, such as normal saline solution, various medicaments and total paternal nutrition, into a patient, withdrawing blood from a patient or monitoring various parameters of the patient's vascular system. Peripheral IV catheters tend to be relatively short, and typically are on the order of about two inches or less in length. The most common type of IV catheter is an over-the-needle peripheral IV catheter. As its name implies, an over-the-needle catheter is mounted over an introducer needle having a sharp distal tip. At least the distal portion of the catheter tightly engages the outer surface of the needle to prevent peelback of the catheter, thereby facilitating insertion of the catheter into the blood vessel. The catheter and the introducer needle are assembled so that the distal tip of the introducer needle extends beyond the distal tip of the catheter, with the bevel of the needle facing up away from the patient's skin.

The catheter and introducer needle assembly is inserted at a shallow angle through the patient's skin into a blood vessel. There are many techniques for inserting such a catheter and introducer needle assembly into a patient. In one insertion technique, the introducer needle and catheter are inserted completely into the blood vessel together. In another technique, the introducer needle is partially withdrawn into the catheter after the initial insertion into the blood vessel. The catheter is then threaded over the needle and inserted completely into the blood vessel.

To verify proper placement of the catheter in the blood vessel, the clinician confirms that there is flashback of blood in a flashback chamber. The flashback chamber is typically formed as part of the needle hub. Alternatively, where the introducer needle includes a notch, i.e., a hole or opening in the sidewall of the introducer needle, flashback of blood can be observed in the annular space between the introducer needle and the catheter, in the catheter adapter and, where the catheter is an integrated catheter, in an extension tube extending from a side arm formed in the catheter adapter. Once proper placement of the catheter into the blood vessel is confirmed, the clinician applies pressure to the blood vessel by pressing down on the patient's skin over the blood vessel distal to the introducer needle and catheter. This finger pressure occludes, or at least minimizes, further blood flow through the introducer needle and the catheter. The clinician then withdraws the introducer needle, leaving the catheter in place, and attaches an appropriate device to the catheter. Such a device can include a fluid delivery device, a PRN, a dead-ender cap or a blood pressure monitoring probe. Once the introducer needle is withdrawn from the catheter, the introducer needle is a "blood contaminated sharp" and must be properly handled.

In recent years, there has been great concern over the contamination of clinicians with a patient's blood and a recognition that blood contaminated sharps must be disposed of to avoid an accidental needle stick. This concern has arisen because of the advent of currently incurable and fatal diseases, such as Acquired Immune Deficiency Syndrome ("AIDS"), which can be transmitted by the exchange of body fluids from an infected person to another person. Thus, contact with the body fluids of an AIDS infected person must be avoided. As noted above, if an introducer needle has been used to place a catheter in a blood vessel of an AIDS infected person, the introducer needle, via its sharp distal tip, is a vehicle for the transmission of the disease. Although clinicians are aware of the need to properly handle blood contaminated sharps, unfortunately, in certain medical environments such as emergency situations or as a result of inattention or neglect, needlesticks with a blood contaminated sharp still occur.

As a result of the problem of accidental needlesticks by blood contaminated sharps, various needle shields have been developed. Such devices are disclosed in, for example, U.S. Pat. Nos. 5,601,536 and 4,952,207. Generally, such needle shields rely on movement and interaction between a projection or fingers and a notch.

It would be desirable to provide a capture and shielding arrangement having an improved capture mechanism.

SUMMARY OF THE INVENTION

It is, therefore, an object of this invention to provide one or more of the following features and advantages: a shield that is compact; a shield that is simple and easy to use; a shield that requires no special features or techniques to be operative; a lock that utilizes an interaction with the sharp that is perpendicular or substantially perpendicular to the longitudinal axis; and a shield that will work regardless of the rotational orientation of the sharp.

According to one aspect, the present invention provides an assembly comprising a sharp defining an outer diameter and a longitudinal axis, a shield, and a lock constructed to provide an interaction with the sharp that is perpendicular or substantially perpendicular to the longitudinal axis, the interaction being effective regardless of the rotational orientation of the sharp. The interaction can be effective to prevent unwanted proximal and distal movement of the sharp relative to the shield. The shield can comprise a cavity through which the sharp extends. The lock may include one or more radially-inwardly directed springs extending from a main body portion, which can be annular. The radially-inwardly directed springs may be sinusoidal, wherein the sinusoid can extend through at least about 450°. The radially-inwardly directed springs comprise innermost edges that can act to define an opening having a diameter less than the outer diameter of the sharp, when in an unbiased condition. The sharp may have a notch, the notch and the radially-inwardly directed springs are constructed such that, as the needle is moved proximally with respect to the shield, at least one of the radially-inwardly directed springs becomes aligned with, and moves into, the notch. The shield may comprise a cavity having at least one radially-extending proximal bearing surface and at least one radially-extending distal bearing surface, the proximal and distal bearing surfaces constructed and arranged for at least partial contact with one or more of the radially-inwardly directed springs.

According to a further aspect, the radially-inwardly directed springs each comprise a plurality of first hinges separated by at least one gap, and at least one second hinge accessible via the gap. The lock may be formed primarily from a polymer, optionally having one or more metal inserts disposed therein. The hinges can be constructed and arranged such that upon application of a force to the at least one second hinge, the innermost edges of the radially-inwardly directed springs are moved thereby in a generally radially-outward direction, and wherein upon removal of the force, the innermost edges are moved in a generally radially-inward direction.

According to yet another aspect, the assembly can additionally include a catheter assembly, the catheter assembly comprising a catheter, and the sharp comprising an introducer needle. The catheter assembly may comprise a catheter adapter, and the catheter can comprise a proximal end and a distal end, the proximal end connected to the catheter adapter. The catheter optionally includes a proximal end and a distal end, the catheter being coaxially disposed over the needle, the distal end of the catheter closely engaging an outer surface of the needle. The catheter assembly may additionally include a side arm having an extension tube in fluid communication with the catheter. The assembly can also include a Y-connector attached to the extension tube, and a fluid control valve and a vent plug attached to the Y-connector.

According to a further aspect, the present invention provides an assembly comprising: a sharp defining and outer diameter and a longitudinal axis; a shield; and means for preventing unwanted proximal and distal movement of the sharp relative to the shield regardless of the rotational orientation of the sharp.

According to still another aspect, the present invention provides a method of preventing unwanted proximal and distal movement of a sharp relative to a shield, the method comprising: providing a lock within the shield, the lock interacting with the sharp in a direction perpendicular or substantially perpendicular to the longitudinal axis, the lack being effective regardless of the rotational orientation of the sharp; introducing the sharp into the shield up to a predetermined position relative to the shield; at which location the interaction between the lock and the sharp prevents further unwanted proximal and distal movement of the sharp within the shield.

BRIEF DESCRIPTION OF THE DRAWINGS

The preferred embodiments are illustrated in the drawings in which like reference numerals refer to the like elements and in which.

DETAILED DESCRIPTION OF THE INVENTION

As used herein, the term "proximal" refers to a location on the catheter and introducer needle assembly with needle shield of this invention that, during normal use, is closest to the clinician using the device and farthest from the patient in connection with whom the device is used. Conversely, the term "distal" refers to a location on the catheter and introducer needle assembly of this invention that, during normal use, is farthest from the clinician using the device and closest to the patient in connection with whom the device is used.

As used herein, the term "top," "up" or "upwardly" refers to a location on the catheter and introducer needle assembly with needle shield of this invention that, during normal use, is radially away from the longitudinal axis of the device and away from the patient's skin. Conversely, as used herein, the term "bottom," "down" or "downwardly" refers to a location on the catheter and introducer needle assembly of this invention that, during normal use, is radially away from the longitudinal axis of the device and toward the patient's skin.

As used herein, the term "in" or "inwardly" refers to a location with respect to the catheter and introducer needle assembly with needle shield of this invention that, during normal use, is toward the inside of the device. Conversely, as used herein, the term "out" or "outwardly" refers to a location with respect to the catheter and introduce needle assembly of this invention that, during normal use, is toward the outside of the device.

As used herein the phrase "unwanted proximal and distal movement" means proximal and distal movement of a needle or sharp with respect to a needle shield that allows the sharp tip to be re-exposed from the needle shield.

As used herein the phrase "perpendicular or substantially perpendicular" is intended to encompass a range of angular relationships from 90° to 90°+/−a slight angular variation. The angular variation may be of a magnitude associated with manufacturing tolerances and inaccuracies. Alternatively, the slight angular variation may be up to 1°, 2°, or even a few degrees.

As used herein the term "sharp" is intended to encompass needles, lancets, and other articles shaped such that they can readily penetrate the skin.

The present invention is described herein using the reference numbers for like elements in the different embodiments. Although this invention is described herein in connection with a peripheral IV catheter having an integrated extension tube (an "integrated catheter"), it is to be understood that this invention is applicable to other devices and arrangements. For example, this invention is applicable to standard IV catheters and extended dwell catheters requiring the needle to be connected to the needle hub by a stylet. More generally, the basic aspects and features of the present invention can be utilized alone or in combination with a number of different devices where it is desirable to shield a sharp.

Figure 1:
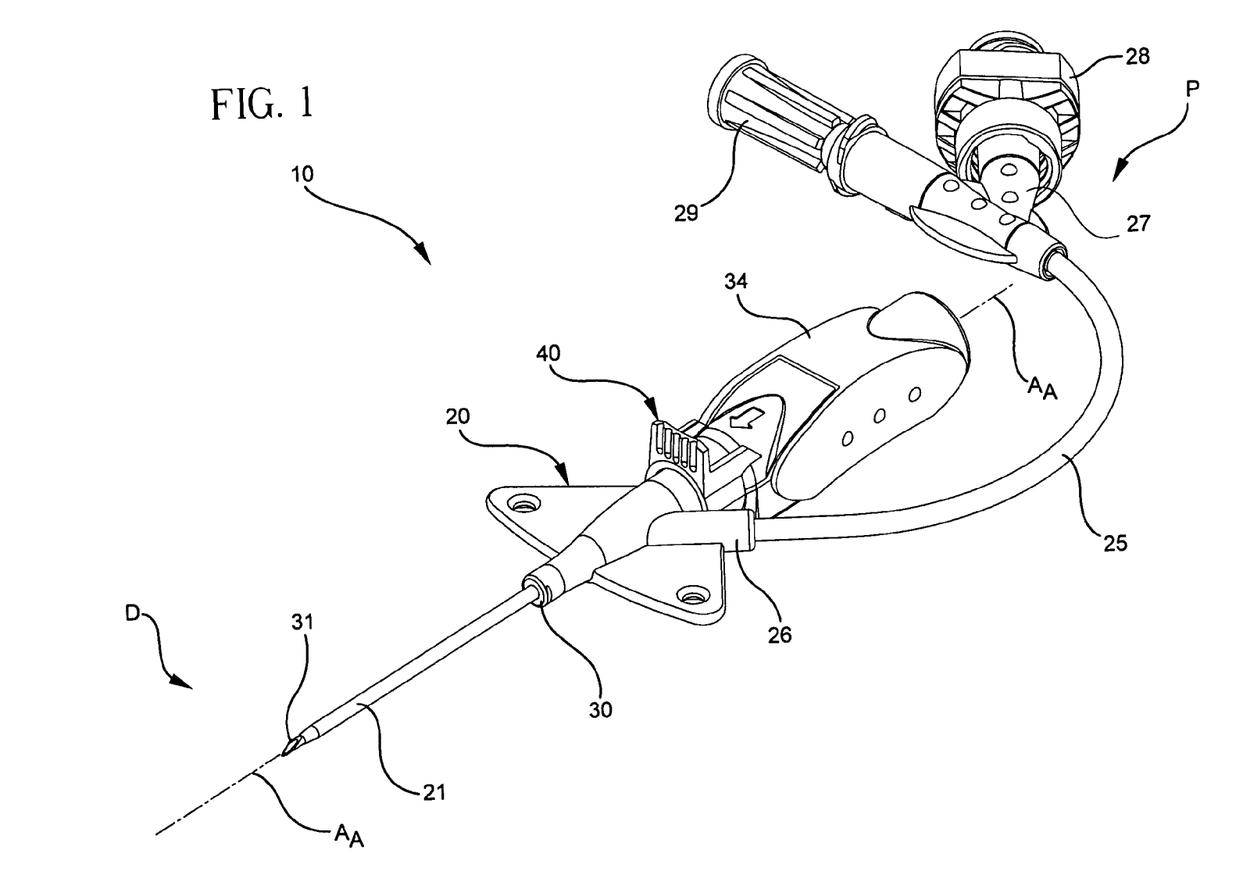
FIG. 1 is a top perspective view of an integrated catheter and introducer needle assembly with an embodiment of the needle shield of this invention.
Figures 2, 2A:
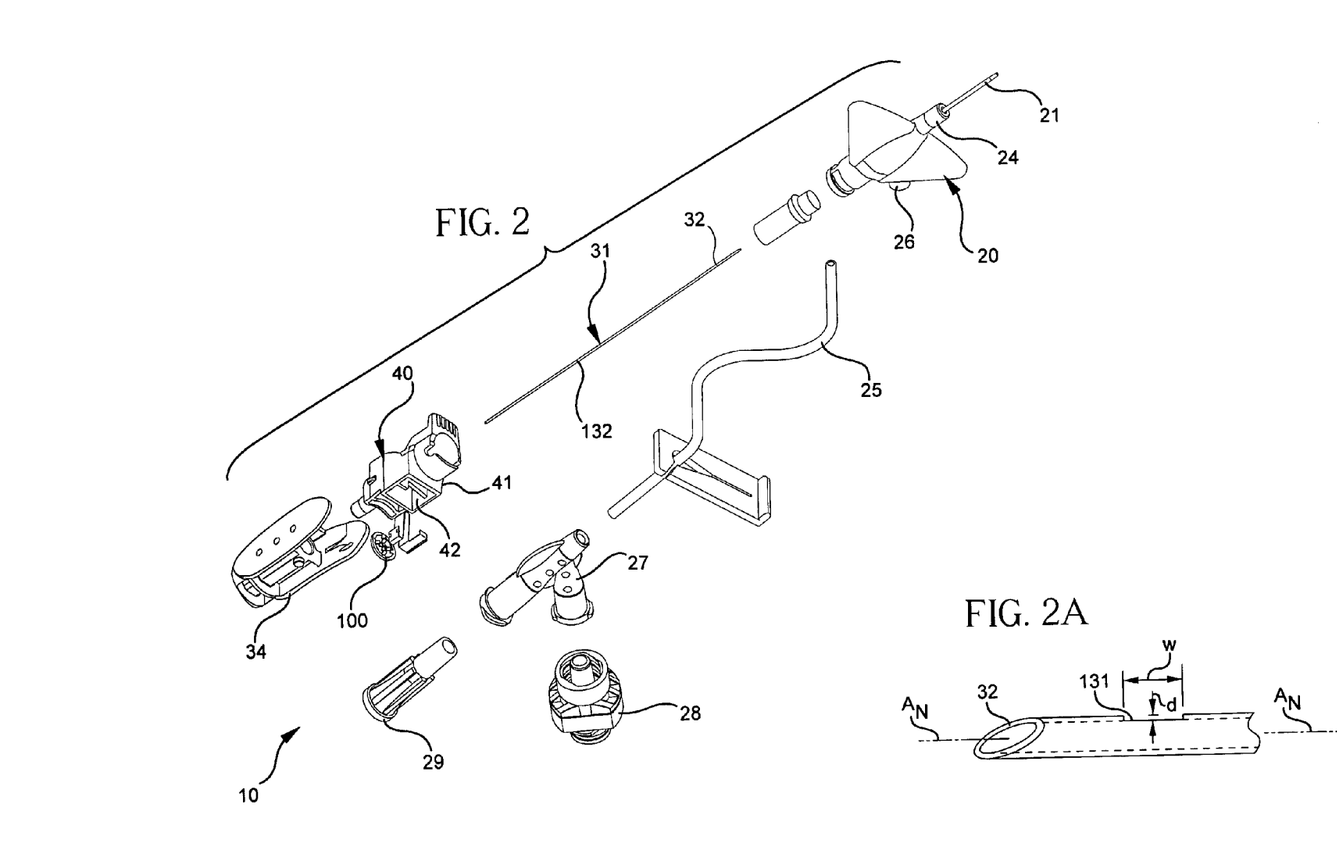
FIG. 2 is an exploded bottom, perspective view of an integrated catheter and introducer needle assembly with an embodiment of the needle shield of this invention.
FIG. 2A is an enlarged perspective view of the proximal end of a preferred embodiment of the introducer needle that is used in the integrated catheter and introducer needle assembly with an embodiment of the needle shield of this invention.

As illustrated in FIGS. 1-2, one example of a catheter and introducer needle assembly according to the present invention is identified generally by the numeral 10 and defines a longitudinal axis $A_A$ extending therethrough. It includes a catheter assembly 20 and an introducer needle assembly 30 that includes a needle shield 40.

Catheter assembly 20 includes a catheter 21 that has a proximal end P, a distal end D and a catheter adapter 24 affixed to the distal end of catheter 21. Suitable materials for catheter 21 include, but are not limited to, thermoplastic resins such as fluorinated ethylene propylene (FEP), polytetrafluoroethylene (PTFE), polyurethane and the like. Preferably, catheter 21 is formed from thermoplastic hydrophilic polyurethane that softens with exposure to physiological conditions present in the patient's body. Suitable materials for catheter adapter 24 include, but are not limited to, thermoplastic polymeric resins such as polycarbonate, polystyrene, polypropylene and the like. Catheter assembly 20 may include an integrated extension tube 25 extending from a side arm 26 on catheter adapter 24. Extension tube 25 may include a Y-connector 27 at its proximal end with a fluid control valve 28 and a vent plug 29 thereon.

In the illustrated embodiment, the introducer needle assembly 30 includes introducer needle 31 having a sharp distal tip 32 defined by a bevel and a proximal end connected to a needle hub 34. As illustrated in FIG. 2A, introducer needle 31 defines a feature such as a notch 131, i.e., a hole or opening formed in the sidewall of introducer needle 31. The feature may be disposed adjacent to the distal end. The feature or notch 131 serves two functions. One function is to allow blood flow from the open distal end of the introducer needle 31 through the notch and into the annular space between the introducer needle 31 and the catheter 21. This allows the clinician to observe flashback of blood in catheter 21, catheter adapter 24 and extension tube 25, if those elements are at least translucent. The other function is to cooperate with a lock associated with the needle shield 40 to prevent unwanted proximal and distal movement of the introducer needle with respect to the needle shield. In other words, the sharp distal tip will not be re-exposed from the proximal end or the distal end of the needle shield 40 once the sharp distal tip 32 has been withdrawn into the needle shield 40 after use. The notch 131 can be provided with any suitable dimensions. For purposes of illustration only, the notch 131 can be provided with a depth d on the order of about 0.0063 inches, or roughly up to one-half outer diameter of the needle 31, and can have a width on the order of about ⅜ max.

Introducer needle 31 is preferably formed from stainless steel and has a longitudinal axis $A_N$ that is generally parallel to the longitudinal axis $A_A$ of catheter and introducer needle assembly. Needle hub 34 may be formed from the same types of materials that are used to form catheter adapter 24. Of course, other materials could be used to form needle hub 34. Any suitable thermoplastic, such as polycarbonate, ABS, polyetherylene, polyuretuane.

Introducer needle assembly 30 also includes needle shield 40, which in turn includes housing 41 defining an internal cavity 42 therein. Housing 41 also defines a proximal opening and a distal opening in communication with internal cavity 42. This allows introducer needle 31 to extend longitudinally through housing 41.

Figure 3:
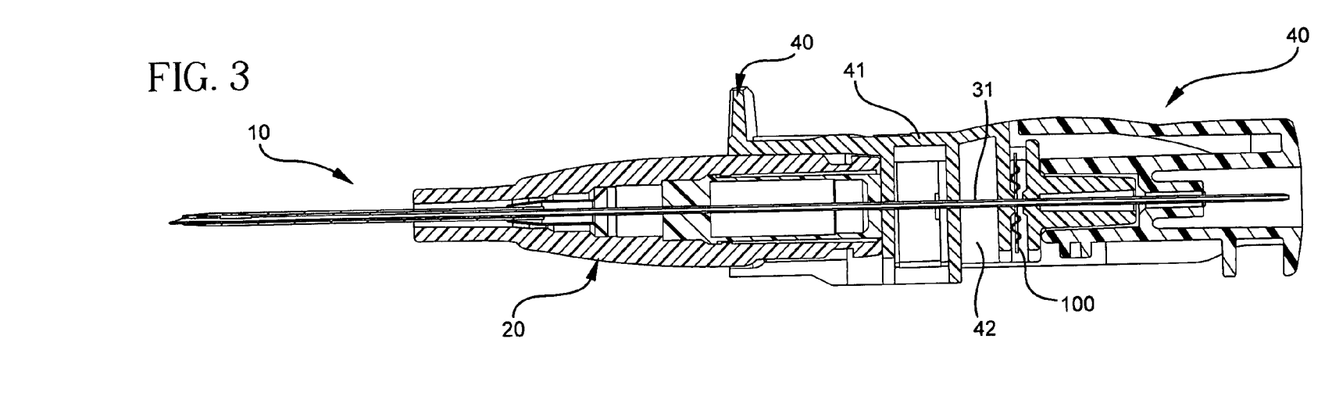
FIG. 3 is a cross-sectional view of the integrated catheter and introducer needle assembly with an embodiment of the needle shield of this invention showing the assembly prior to use.
Figure 4:
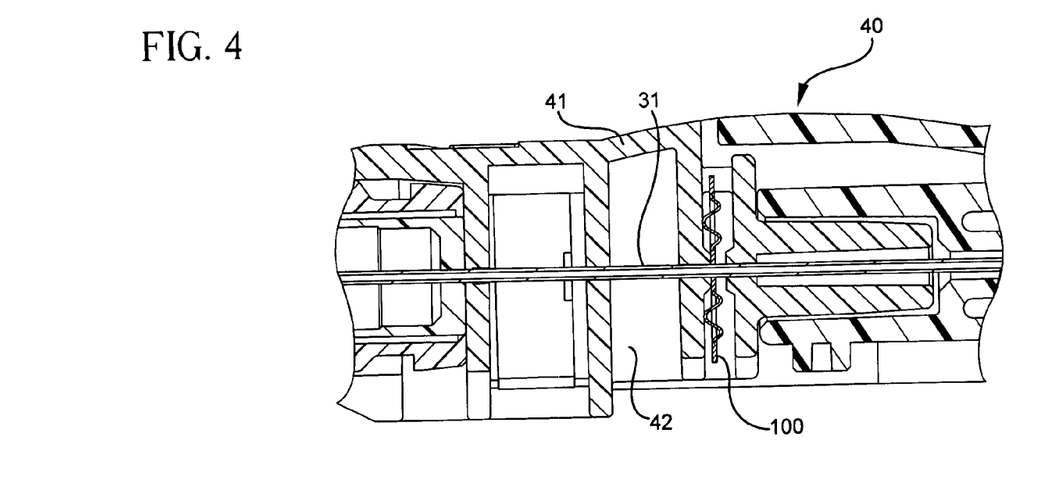
FIG. 4 is an enlarged cross-sectional view of a portion of the integrated catheter and introducer needle assembly with the needle shield of FIG. 3.
Figure 5:
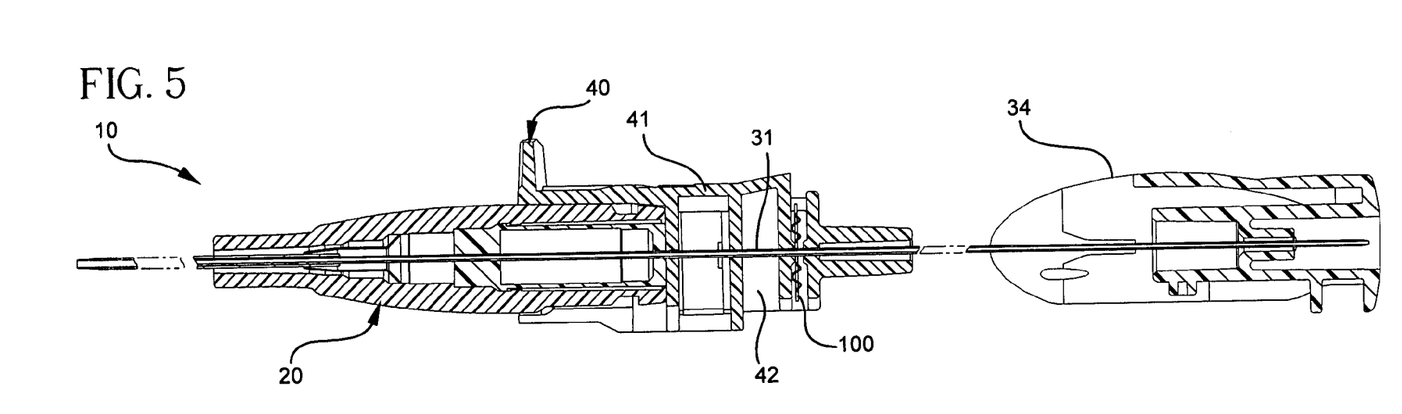
FIG. 5 is a cross-sectional view of the integrated catheter and introducer needle assembly with an embodiment of the needle shield of this invention showing the introducer needle withdrawn from the catheter and disposed in the needle shield.
Figure 6:
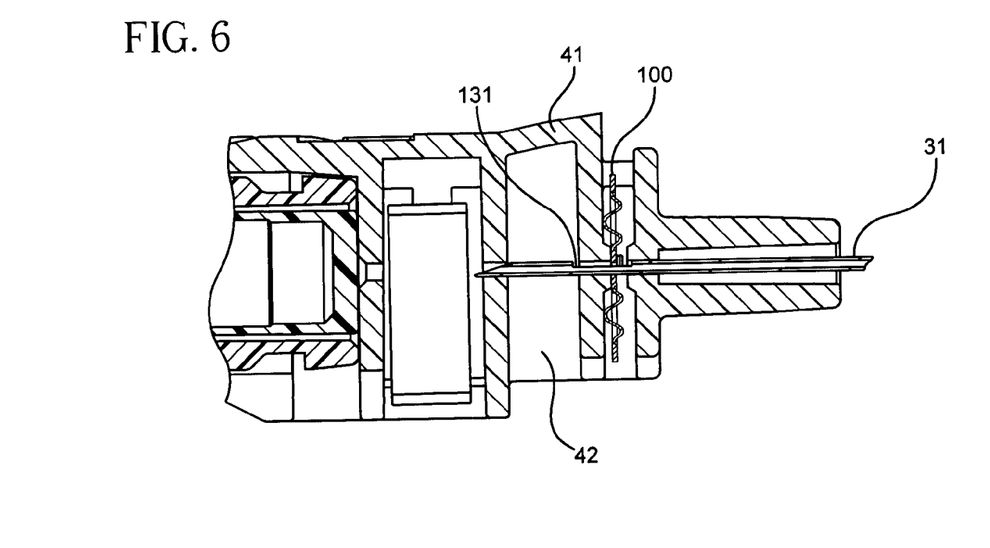
FIG. 6 is an enlarged cross-sectional view of a portion of the integrated catheter and introducer needle assembly with the needle shield of FIG. 5.

FIGS. 3-4 illustrate the positions of the various components of the integrated catheter and introducer needle assembly 10 prior to use. FIGS. 5-6 illustrate the positions of the various components of the assembly 10 when the introducer needle 31 is withdrawn into the needle shield 40.

An assembly formed according to the principles of the present invention comprises means to prevent unwanted proximal and distal movement of the needle 31, or other sharp, relative to the shield. The means may be effective regardless of the rotational orientation of the needle 31, or other sharp. The means may also provide an interaction with needle 31, or other sharp, that is perpendicular, or substantially perpendicular to the longitudinal axis. The above-described means may comprise any of the locks of the embodiments described below, and may further comprise a feature on the needle 31, or other sharp, such a notch (131), opening or hole.

As illustrated in FIGS. 7-10, a lock 100 that prevents unwanted proximal and distal movement of the introducer needle 31, or other sharp, is disposed in pocket 43 of cavity 42. Locating the lock 100 adjacent to a radially-directed proximal bearing surface 44 and a radially-directed distal bearing surface 45 in pocket 43 ensures that the radial and axial forces on lock 100 are balanced so that the lock 100 remains substantially perpendicular to introducer needle 31.

Figure 7:
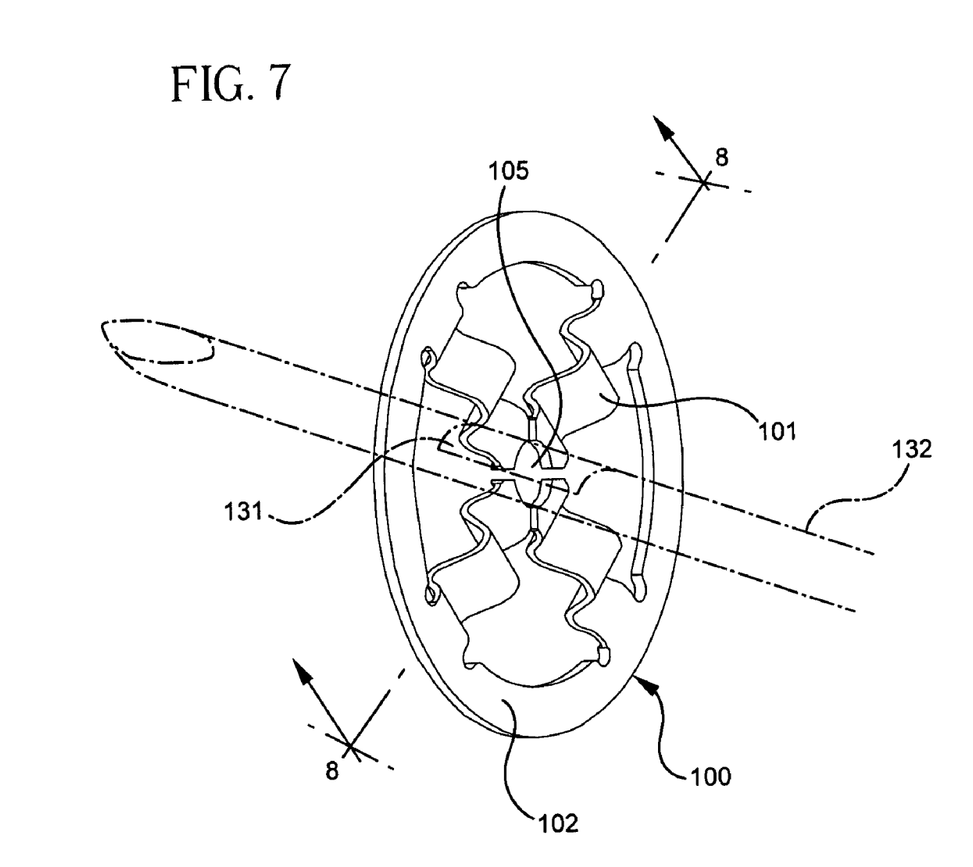
FIG. 7 is a perspective view of one embodiment of a lock with an introducer needle shown in phantom.
Figure 8:
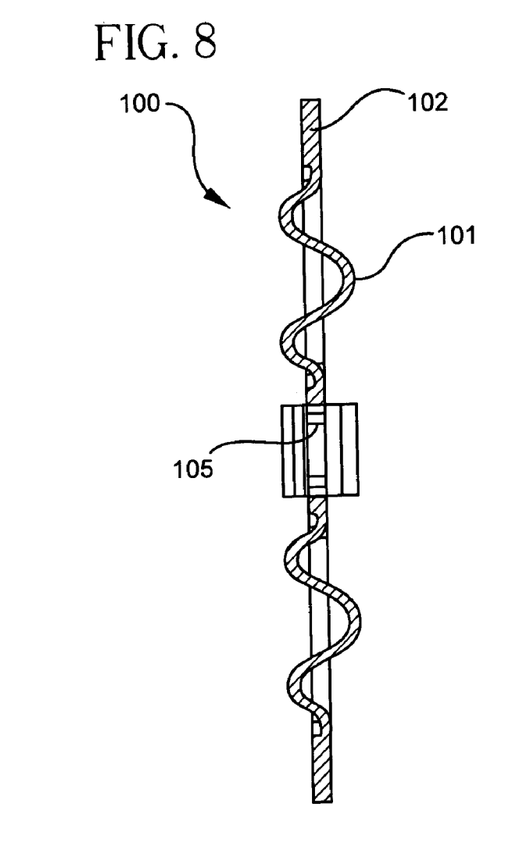
FIG. 8 is a cross-sectional view of the lock of FIG. 7 taken along line 8-8.

As best illustrated in FIGS. 7-8, the lock 100 can take the form of a disk-like member having one or more radially-inwardly directed springs 101 formed around and extending inwardly from the main body 102. Preferably main body 102 has an annular configuration with four springs 101 equiangularly located about main body 102. Each spring member 101 is formed from a rectangular strip material that is bent into corrugated, i.e., substantially sinusoidal, configuration. Preferably, the sine wave extends through about 450 degrees. The thickness of the corrugated portion is preferably about 0.003-0.010 inches. In the unbiased condition, the innermost edges of springs 101 define an opening 105 therebetween that has a diameter smaller than the outer diameter of introducer needle 31. Thus, springs 101 are moved radially outwardly to provide space for introducer needle 31 when introducer needle 31 is placed in opening 105 during assembly. Thus, springs 101 have a bias for radial inward movement. As introducer needle 31 is withdrawn into needle shield 40, the main portion 132 of introducer needle 31 rides past springs 101 with the above-described interference. As introducer needle 31 continues to move proximally with respect to needle shield 40, notch 131 will become aligned with springs 101 such that at least one of the springs 101 will move radially inwardly into notch 131. The lock 100 can be formed from any suitable material, such as a metal. For instance, 300 or 400 series stainless steel in an exemplary material.

Figure 9:
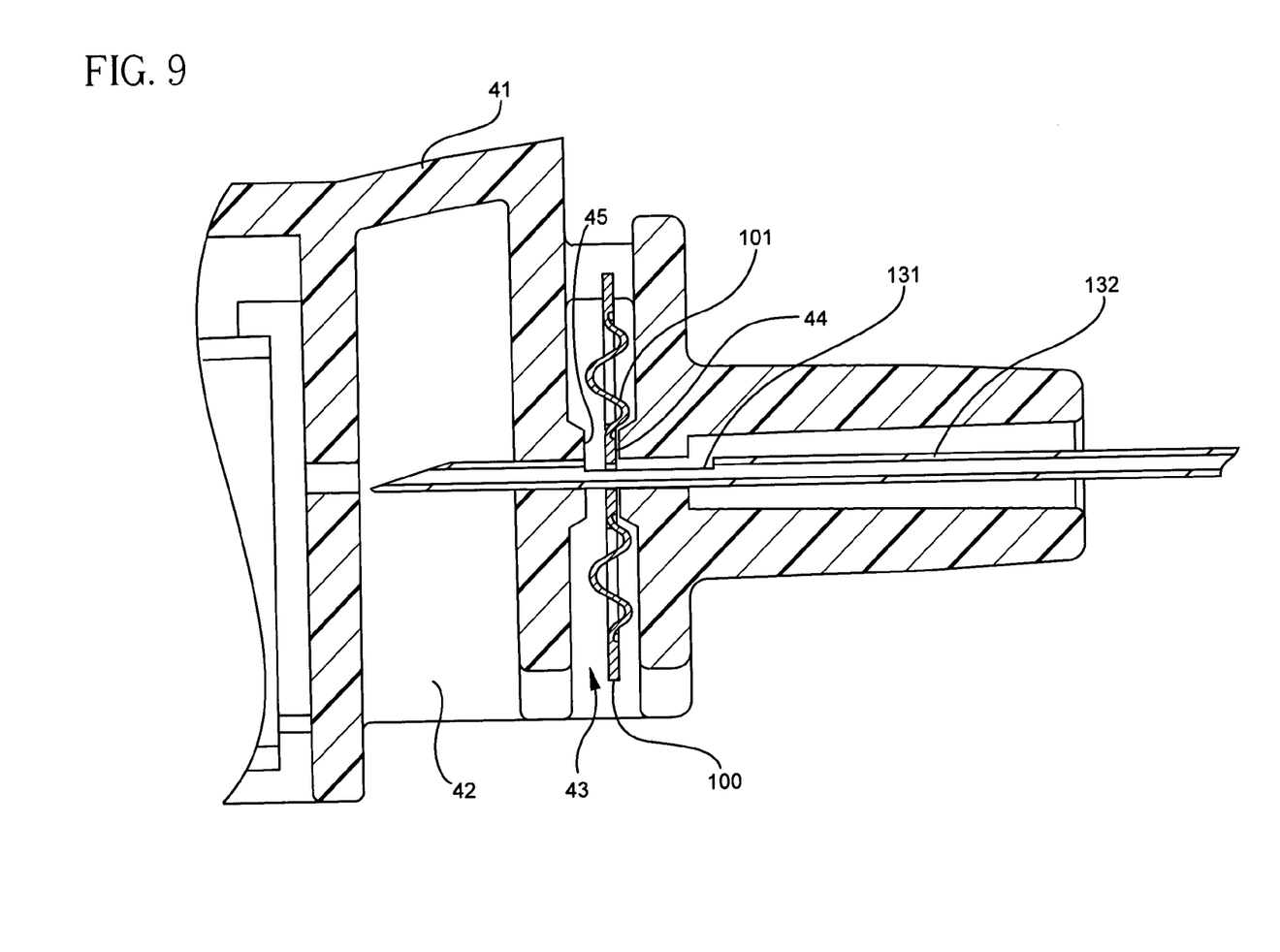
FIG. 9 is an enlarged cross-sectional view of a portion of the integrated catheter and introducer needle assembly with the needle shield of this invention similar to that shown in FIG. 6, but further enlarged to show the relationship between the lock and the introducer needle, wherein the spring member is preventing further proximal movement of the introducer needle.
Figure 10:
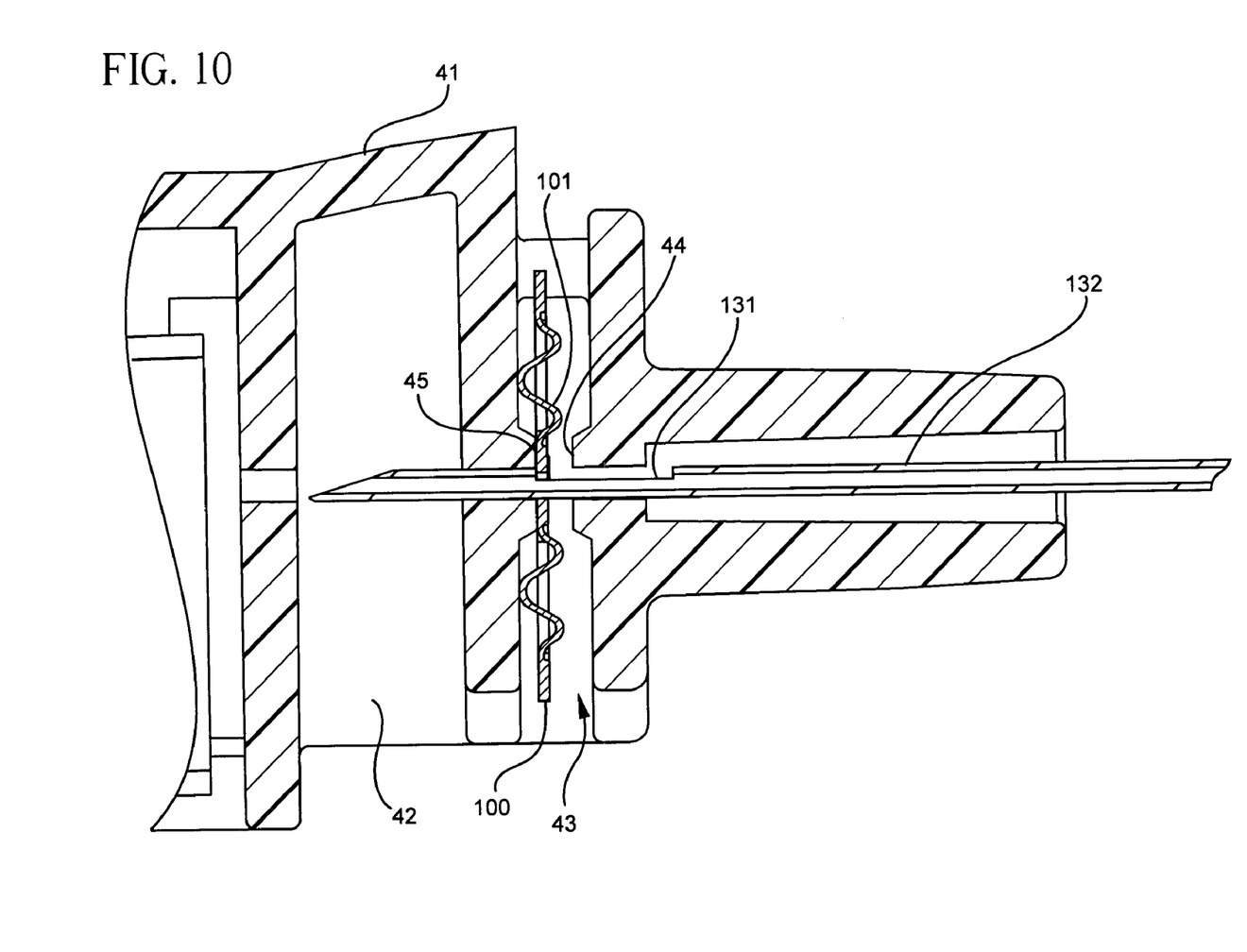
FIG. 10 is an enlarged cross-sectional view of a portion of the integrated catheter and introducer needle assembly with the needle shield of this invention similar to that shown in FIG. 9, but showing the relationship between the lock and the introducer needle, wherein the spring member is preventing further distal movement of the introducer needle.

As illustrated in FIGS. 9-10, continued proximal movement of introducer needle 31 will cause the spring 101 to engage the distal end of notch 131 and prevent any subsequent proximal movement of introducer needle 31. Similarly, distal movement of the introducer needle 31 will be prevented when the spring 101 engages the proximal end of notch 131. Even if introducer needle 31 is rotated when it is pulled proximally or pushed distally, lock 100 still restrains introducer needle 31 against unwanted proximal and distal movement. This allows lock 100 to be effective no matter what the rotational orientation of the introducer needle 31. The above-described arrangement provides strong resistance to this unwanted proximal and distal movement. Strength is provided, at least in part, by minimization of the lever arm defined by the contact between bearing surfaces 44 and 45, the springs 101, and the proximal and distal ends of the notch 131.

During assembly of introducer needle assembly 30, the lock 100 should be properly aligned in needle shield 40 and with respect to introducer needle 31. For example, the lock 100 and introducer needle 31 should be concentric with a tolerance of no more than about 0.0002 inches. To properly place introducer needle 31 into opening 105 so that the desired concentricity results, the proximal end of introducer needle 31 is inserted through the distal end of lock 100. In addition, the proximal end of introducer needle 31 can be tapered (not shown) with the smallest portion of the taper having a diameter of about 0.0025 inches to about 0.0050 inches less than the diameter of opening 105. The diameter of opening 105 can be between about 0.006 inches and about 0.010 inches smaller than the diameter of introducer needle 31. This will cause springs 101 to become biased to move radially inward when introducer needle 31 is placed in opening 105. Springs 101 should be compressed by a suitable amount, such as at least about 0.003 inches to about 0.005 inches so that there will be radial movement of springs 101 into notch 131.

As previously mentioned, the radially-directed bearing surfaces 44, 45 balance the radial and axial forces generated during assembly and activation and guide the movement of the springs 101, such that the spring movement is as close to purely perpendicular to the longitudinal axis $A_N$ as possible.

Once sharp distal tip 32 of introducer needle 31 has been withdrawn into needle shield 40 so that lock 100 engages notch 131 to prevent unwanted proximal and distal movement of introducer needle 31, needle shield 40 can be disconnected from catheter adapter 24. Thereafter, the clinician may attach a fluid delivery device, a PRN, a deadender cap or some other blood monitoring device to extension tube 25 and commence the planned treatment.

Introducer needle 31 and needle shield 40 may then be disposed of according to the facility's disposal protocol. Alternatively, such devices may be connected to extension tube 25 prior to venipuncture.

An alternative embodiment of the present invention is illustrated in FIGS. 11-14C. As illustrated therein, according to this second embodiment, the lock is provided with an alternative construction. It should be noted that the lock member of this alternative embodiment may be combined with surrounding members, and utilized in a similar fashion, to that described above in connection with the embodiment depicted and described in connection with FIGS. 1-10.

Figure 11:
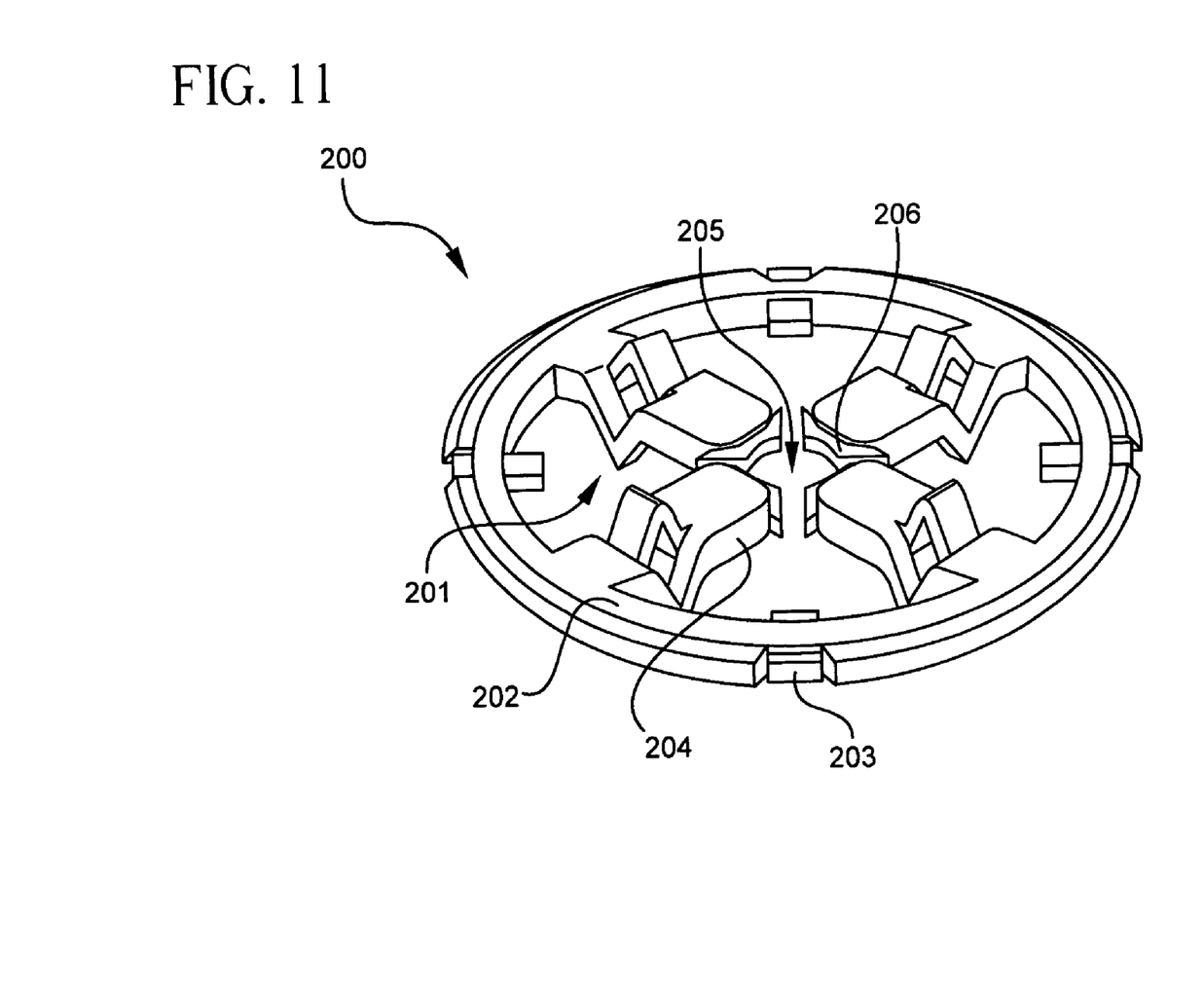
FIG. 11 is a perspective view of a second embodiment of a lock constructed according to the principles of the present invention.

As illustrated in FIG. 11, the lock 200 can generally take the form of a disk-like member with a plurality of radially-inwardly directed springs 201 formed around and extending inwardly from a main body portion 202. According to the illustrated embodiment, the main body portion 202 may include one or metal reinforcements 203. Each of the plurality of radially-inwardly directed springs 201 includes a radially inward portion 204 defining an opening 205 therein. The opening 205 is adapted to receive needle or cannula 31, such as that previously described. According to the illustrated embodiment, the radially inward portion of each spring 201 may comprise a metal insert 206.

Figure 12A:
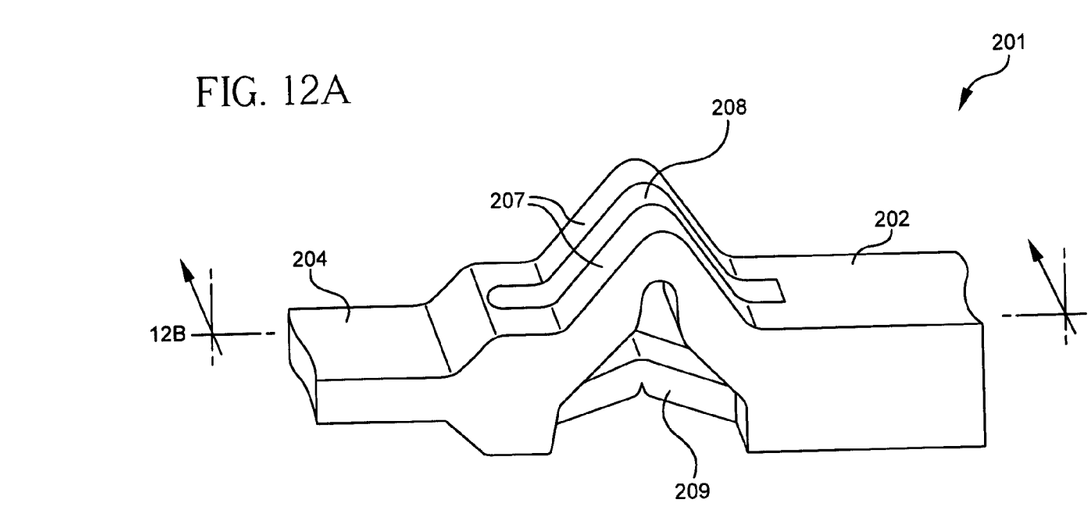
FIG. 12A is a perspective view of a portion of the lock illustrated in FIG. 11.
Figure 12B:
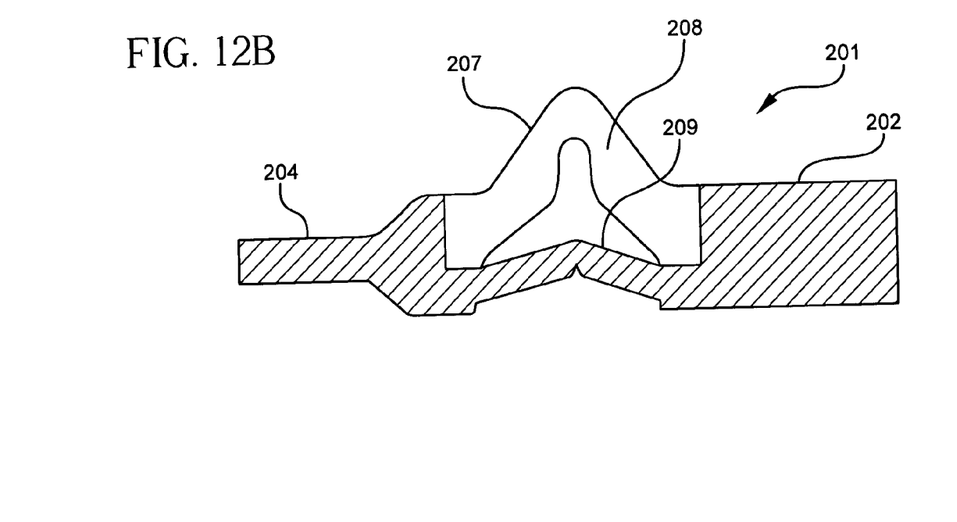
FIG. 12B is a sectional view taken along line 12B-12B of FIG. 12A.

Further detail of the construction of each of the springs 201 is illustrated in FIG. 12A. As illustrated therein, each of the springs 201 generally comprises an arrangement of hinges interconnecting the main body portion 202 with the radially inward portion 204. According to the illustrated embodiment, the arrangement of hinges includes a first plurality of hinges 207 defining a gap 208 therebetween. The arrangement further includes at least one additional, or second hinge 209. Preferably, second hinge 209 is accessible via the gap 208 between the plurality of first hinges 207. It should be understood the above-described hinge arrangement is that of a preferred embodiment, but which could be readily modified by those of ordinary skill in the art in order to achieve the same objective.

Figure 13A:
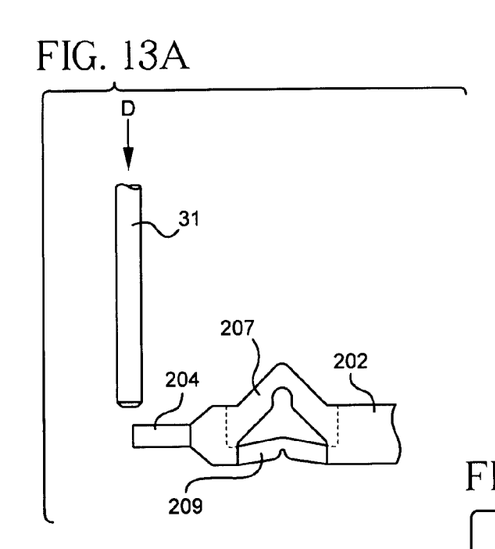
FIGS. 13A-13C illustrate a mode of operation of the lock constructed according to the second embodiment of the present invention.
Figure 13B:
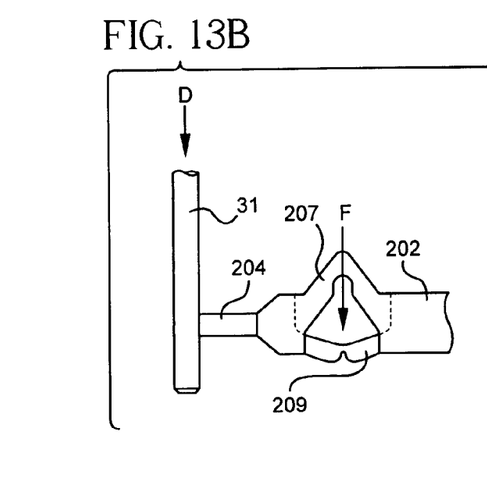

A mode of operation of a hinge constructed as described above is illustrated in FIGS. 13A-13C. As illustrated in FIG. 13A, in a normal, unstressed state, the inner diameter of the radially inward portion 204 of the spring 201 is smaller than the outer diameter of the needle or cannula 31. FIG. 13B depicts application of a force F to the second hinge 209. Application of the force F causes the hinge 209 to extend along the direction indicated by arrow F, which in turn causes the radially-inward portion 204 of the spring 201 to travel in the generally radially outward direction. Thus, by application of force F, the spring 208 is preloaded, and sufficient clearance is created to enable the cannula or needle 31 to pass through the central opening 205 of the lock 200. The force F can be applied by any suitable means. For example, the force F may be applied by a probe or tool that is inserted into the gap 208 between the plurality of first hinges so that it comes into contact with an upper surface of the second hinge 209, as illustrated in FIG. 13B. Other mechanisms for generating force F are contemplated, such as differential air pressures and movement caused by thermal expansion or contraction.

Figure 13C:
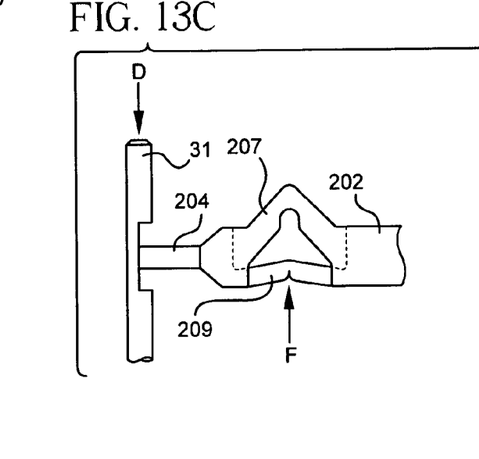

As illustrated in FIG. 13C, upon reaching a suitable capture mechanism, such as notch 131, the force F is removed from the second hinge 209, thus resulting in movement of the hinge in the direction indicated by arrow, which in turn results in a radially-inward movement of the radially-inward portion 204. Thus, in the state depicted in FIG. 13C, the needle or cannula 31 is trapped or positively located by the above-described action of the lock 200.

Figure 14A:
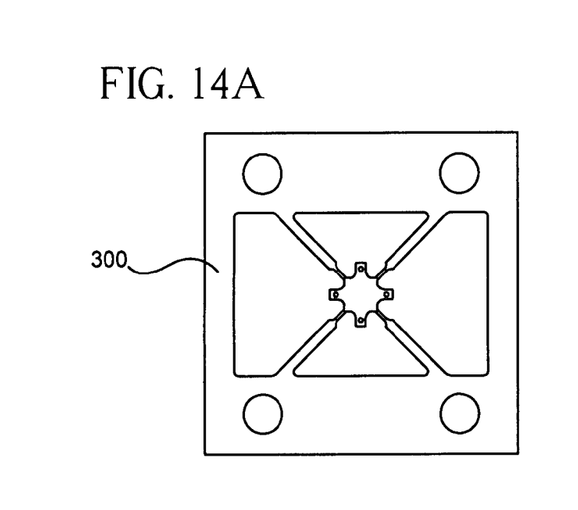
FIGS. 14A-14C illustrate an exemplary technique for constructing the lock of the second embodiment of the present invention.
Figure 14B:
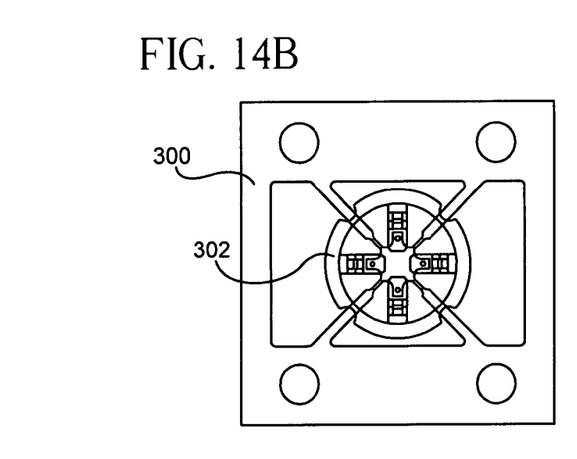
Figure 14C:
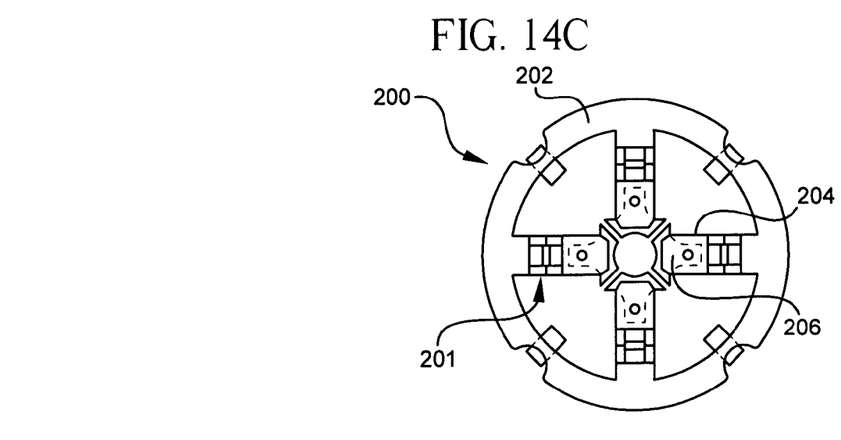

The lock 200 may be constructed by any suitable technique. An illustrative technique for constructing the lock member 200 will now described by reference to FIGS. 14A-14C. As illustrated in FIG. 14A, a patterned metal sheet 300 is formed by any suitable material removal technique. The sheet 300 is then fed into an insert molding machine (not shown) where the plastic portion 302 of the lock 200 is molded over previously described metal sheet 300. Next, suitable material removal technique, such as stamping, is then performed on the molded piece of FIG. 14B to remove the unwanted portions of the metal sheet 300. This step is illustrated in FIG. 14C. It should be understood that the above-described technique is exemplary in nature, and alternative techniques for forming the lock 200 may be employed by those skilled in the art. The lock 200 may be constructed of a number of different suitable materials. For example, the metal and plastic materials may comprise any of the metal or polymeric materials previously identified herein.

Thus, it is seen that a catheter and introducer needle assembly with needle shield is provided that is compact, simple and easy to use, requires no special features or technique to be operative and works no matter what the rotational orientation of the introducer needle.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

I claim:

1. An assembly comprising:
a sharp defining an outer diameter and a longitudinal axis, the sharp has a notch with a first shoulder and a second shoulder that are perpendicular or substantially perpendicular to the longitudinal axis, the notch extending along the longitudinal axis;
a shield; and
a disk-like lock having a main body portion that forms an outer frame and radially-inwardly directed compression springs that have outer ends attached to the main body and inner ends that define a central opening through which the sharp extends, the compression springs being radially-inwardly directed perpendicular or substantially perpendicular to the longitudinal axis of the sharp to provide an abutting interaction with both the first shoulder of the notch to prevent unwanted proximal movement of the sharp relative to the shield and the second shoulder of the notch to prevent unwanted distal movement of the sharp relative to the shield, the interaction being effective regardless of the rotational orientation of the sharp.

2. The assembly of claim 1, wherein the shield comprises a cavity though which the sharp extends.

3. The assembly of claim 1, wherein the main body portion is annular.

4. The assembly of claim 1, wherein the radially-inwardly directed springs are sinusoidal.

5. The assembly of claim 4, wherein the sinusoid extends though at least about 450°.

6. The assembly of claim 1, wherein the central opening has a diameter less than the outer diameter of the sharp when in an unbiased condition.

7. The assembly of claim 1, wherein the lock is at least partially constructed of stainless steel.

8. The assembly of claim 1, wherein the shield comprises a cavity having at least one radially-extending proximal bearing surface and at least one radially-extending distal bearing surface, the proximal and distal bearing surfaces constructed and arranged for at least partial contact with one or more of the radially-inwardly directed springs.

9. An assembly comprising:
a sharp defining an outer diameter and a longitudinal axis;
a shield; and
a lock constructed with one or more radially-inwardly directed springs extending from a main body portion to provide an interaction with a sidewall of the sharp that is perpendicular or substantially perpendicular to the longitudinal axis, the interaction being effective regardless of the rotational orientation of the sharp, the interaction is effective to prevent unwanted proximal and distal movement of the sharp relative to the shield;
wherein the radially-inwardly directed springs each comprise a plurality of first hinges separated by at least one gap, and at least one second hinge accessible via the gap.

10. The assembly of claim 9, wherein the lock is formed primarily from a polymer.

11. The assembly of claim 10, wherein the lock comprises a one or more metal inserts embedded therein.

12. The assembly of claim 9, wherein the hinges are constructed and arranged such that upon application of a force to the at least one second hinge, innermost edges of the radially-inwardly directed springs are moved thereby in a generally radially-outward direction, and wherein upon removal of the force, the innermost edges are moved in a generally radially-inward direction.

13. The assembly of claim 1, further comprising a catheter assembly, the catheter assembly comprising a catheter, and the sharp comprising an introducer needle.

14. The assembly of claim 13, wherein the catheter assembly comprises a catheter adapter, and the catheter comprises a proximal end and a distal end, the proximal end connected to the catheter adapter.

15. The assembly of claim 13, wherein the catheter comprises a proximal end and a distal end, the catheter is coaxially disposed over the needle, the distal end of the catheter closely engaging an outer surface of the needle.

16. The assembly of claim 13, wherein the catheter assembly comprises a side arm having an extension tube in fluid communication with the catheter.

17. The assembly of claim 16, further comprising a Y-connector attached to the extension tube, and a fluid control valve and a vent plug attached to the Y-connector.

18. An assembly comprising:
a sharp defining an order diameter and a longitudinal axis, the sharp having a shoulder that is perpendicular or substantially perpendicular to the longitudinal axis;
a shield; and
a lock having a frame and sinusoidal springs with outer ends attached to the frame, inner ends configured to engage the sharp, and a radially compressible resilient section between the inner and outer ends, the inner end of one of the springs engages the sharp at an angle that is substantially perpendicular to the longitudinal axis and abuttingly interacts with the shoulder to prevent unwanted proximal and distal movement of the sharp relative to the shield.

19. The assembly of claim 18, wherein the radially compressible resilient section includes a sinusoid that extends through at least about 450°.

20. The assembly of claim 18, wherein the sharp comprises a notch, and wherein the notch and the springs are constructed such that, as the needle is moved proximally with respect to the shield, at least one of the springs becomes aligned with, and moves into, the notch.

21. The assembly of claim 18, wherein the springs have innermost edges that define an opening having a diameter less than the outer diameter of the sharp when in an unbiased condition.

22. A method of preventing unwanted proximal and distal movement of a sharp relative to a shield, the method comprising:

provides a lock within the shield, the lock has radially-inwardly directed compression springs having inner ends which engage the sharp in a direction perpendicular or substantially perpendicular to a longitudinal axis of the sharp, the radially-inwardly directed compression springs each comprise a plurality of first hinges separated by at least one gap, and at least one second hinge accessible via the gap, and wherein the hinges are constructed and arranged such that upon application of a force to the at least one second hinge, innermost edges of the radially-inwardly directed springs are moved thereby in a generally radially-outward direction, and wherein upon removal of the force, the innermost edges are moved in a generally radially-inward direction;

introducing the sharp into the shield up to a predetermined position relative to the shield, at which location the abutting interaction between the inner end of one of the springs and perpendicularly oriented shoulders of a notch in the sharp prevents further unwanted proximal and distal movement of the sharp within the shield.

23. The assembly of claim 1, wherein the radially-inwardly directed compression springs each comprise a plurality of first hinges separated by at least one gap, and at least one second hinge accessible via the gap, and wherein the hinges are constructed and arranged such that upon application of a force to the at least one second hinge, innermost edges of the radially-inwardly directed springs are moved thereby in a generally radially-outward direction, and wherein upon removal of the force, the innermost edges are moved in a generally radially-inward direction.

* * * * *

UNITED STATES PATENT AND TRADEMARK OFFICE
CERTIFICATE OF CORRECTION

PATENT NO. : 7,635,352 B2  Page 1 of 1
APPLICATION NO. : 11/138215
DATED : December 22, 2009
INVENTOR(S) : Chad Adams It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 985 days.

Signed and Sealed this

Twenty-first Day of December, 2010

David J. Kappos
*Director of the United States Patent and Trademark Office*